United States Patent [19]

Pallos

[11] Patent Number: 5,232,899
[45] Date of Patent: Aug. 3, 1993

[54] BENZOXAZOLINONES AND THEIR USE AS HERBICIDES

[75] Inventor: Ferenc M. Pallos, Walnut Creek, Calif.

[73] Assignee: Imperial Chemical Industries plc, London, United Kingdom

[21] Appl. No.: 894,883

[22] Filed: Jun. 8, 1992

[51] Int. Cl.$^5$ .................. A01N 43/40; C07D 413/04
[52] U.S. Cl. .................. 504/252; 504/270; 546/270; 548/221
[58] Field of Search .......... 546/270; 548/221; 71/94, 88; 504/252, 270

[56] References Cited

U.S. PATENT DOCUMENTS

| | | | |
|---|---|---|---|
| 4,282,029 | 8/1981 | D'Amico | 546/270 |
| 5,062,884 | 11/1991 | Plath | 71/95 |
| 5,102,898 | 4/1992 | Hsu | 71/67 |

FOREIGN PATENT DOCUMENTS 477819  4/1992  European Pat. Off.

OTHER PUBLICATIONS

Sheradsky CA 89: 215275s, 1978.
CA 55: 16525g 1961 and CA 106(7) 50128a 1987.

*Primary Examiner*—Jane T. Fan
*Attorney, Agent, or Firm*—Lynn Marcus-Wyner

[57] ABSTRACT

A herbicidal substituted benzoxazolinones of the formula

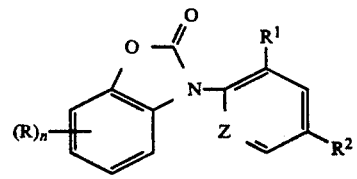

in which:
  R is hydrogen, alkyl, alkoxy, alkenyloxy, alkynyloxy, carboxyalkoxy, alkoxycarbonylalkoxy, alkoxyalkoxy, cyanoalkoxy, haloalkysulphonylamino, alkysulphonylamino, alkoxycarbonyl, haloalkyl, halogen, nitro, carboxy, carboxyalkyl, hydroxy, benzyloxy and cyano;
  n is 0, 1, 2, or 3;
  $R^1$ is hydrogen, nitro, halogen, cyano, haloalkyl, alkyl, alkyoxy, and alkythio;
  $R^2$ is hydrogen, halogen, haloalkyl, haloalkyoxy, nitro and cyano; and
  Z is N or C—$R_3$, wherein $R_3$ is hydrogen, halogen, nitro, cyano, alkythio, alkoxy and haloalkyl. Also disclosed is an herbicidal composition and method of treating weeds.

21 Claims, No Drawings

BENZOXAZOLINONES AND THEIR USE AS HERBICIDES

BACKGROUND AND SUMMARY OF THE INVENTION

This invention relates to substituted benzoxazolinones, a process for producing them and their use as herbicides. In particular this invention relates to substituted benzoxazolinones of the formula

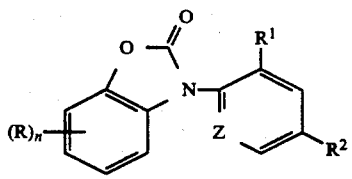

in which:

R is hydrogen, alkyl, alkoxy, alkenyloxy, alkynyloxy, carboxyalkoxy, alkoxycarbonylalkoxy, alkoxyalkoxy, cyanoalkoxy, halogen, nitro, carboxy, carboxyalkyl, hydroxy, benzyloxy, cyano; alkoxycarbonyl, haloalkyl; alkysulphonylamino and haloalkylsulphonylamino n is 0, 1, 2, or 3;

$R^1$ is hydrogen, nitro, halogen, cyano, haloalkyl, alkyl, alkyoxy, and alkythio;

$R^2$ is hydrogen, halogen, haloalkyl, haloalkyoxy, nitro and cyano; and

Z is N or C—$R_3$, wherein $R_3$ is hydrogen, halogen, nitro, cyano, alkythio, alkoxy and haloalkyl; and agriculturally acceptable salts thereof.

DESCRIPTION OF THE INVENTION

Within the scope of the above formula, certain embodiments are preferred, as follows:

R is preferably halogen, nitro, alkyl, alkoxy, amino, alkoxycarbonyl, carboxyalkoxy and alkoxycarbonylalkoxy. Particularly preferred groups are halogen, alkoxy and alkyl. More particularly preferred groups are fluoro, chloro, methoxy and methyl;

n is preferably 1 or 2; and substituted at the 4-, 5- or 6-position.

$R^1$ is halogen. Particularly preferred is chloro and fluoro.

$R^2$ is haloalkyl. Particularly preferred is trifluoromethyl.

Z is preferably N or C-halogen. Particularly preferred when Z is C—$R_3$ is $R_3$ is chloro.

The term "alkyl" and all groups containing alkyl portions are intended to include straight-chain, branched-chain and cyclic groups. Examples are methyl, ethyl, n-propyl, isopropyl, cyclopropyl, n-butyl and t-butyl. Each alkyl member may contain one to six carbon atoms. For example $(C_1-C_6)$alkoxy$(C_1-C_6)$alkoxy.

In the above definitions the term "halogen" includes fluoro, chloro, bromo and iodo groups. In poly halogenated groups the halogens may be the same or different. The term haloalkyl refers to the alkyl group substituted by one or more halogen atoms.

The compounds of the present invention, have been found to be active herbicides, possessing utility as pre-emergence and post-emergence herbicides and useful against a wide range of plant species including broadleaf and grassy species.

This invention therefore also relates to a method for controlling undesirable vegetation comprising applying to a locus where control of such vegetation is desired, either prior or subsequent to the emergence of such vegetation, a herbicidally effective amount of a compound as described herein, together with an inert diluent or carrier suitable for use with herbicides.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn and dwarfing. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots and above-ground portions.

The compounds of this invention are prepared by the following procedures:

GENERAL METHOD OF PREPARATION

The benzoxazolinones as starting materials of the present invention are not novel and can generally be prepared by methods familiar to one skilled in the art, or in the alternative, they can be purchased. The benzoxazolinones then can be arylated on the nitrogen in the presence of bases, such as sodium hydride or potassium carbonate with an appropriate haloaryl or halo-heteroaryl group.

The following examples teach the synthesis of a representative compound of this invention.

EXAMPLE 1

6-fluoro-3-(2',6'-dichloro-4'-trifluorophenyl)-2-benzoxazolinone Compound 15 in Table I

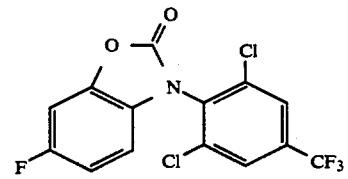

Step 1: Preparation of the intermediate; 6-fluoro-2benzoxazolinone

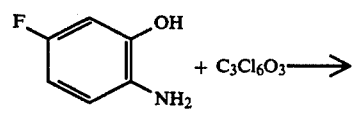

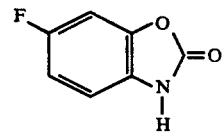

2-amino-5-fluorophenol [4.0 grams (g) (0.03 moles) (M)] was dissolved in 40.0 ml pyridine. The mixture was cooled with an ice bath while triphosgene [3.5 g (0.03 M)] was added. The mixture was heated to 60° C. for 3.0 hours. Thin layer chromatography showed that some of the starting phenol was still present. The mixture was then cooled; triphosgene [0.35 g 0.003 M)] was added and heated to reflux for 4.0 hours. The mixture was cooled, methylene chloride and 10% hydrogen chloride solution was added and stirred to room temperature.

The organic phase was separated, washed with 10% hydrogen chloride solution and with water. The sample was dried over anhydrous magnesium sulfate and stripped under vacuum to yield: 2.2 g dark solid with a melting point of 185-187° C. Spectroscopic data: nuclear magnetic resonance (NMR), C-13 NMR, infrared, and mass spectroscopy are consistent with the proposed structure as 6-fluoro-2-benzoxazolinone.

Step 2: Arylation of the 6-fluoro-2-benzoxazolinone

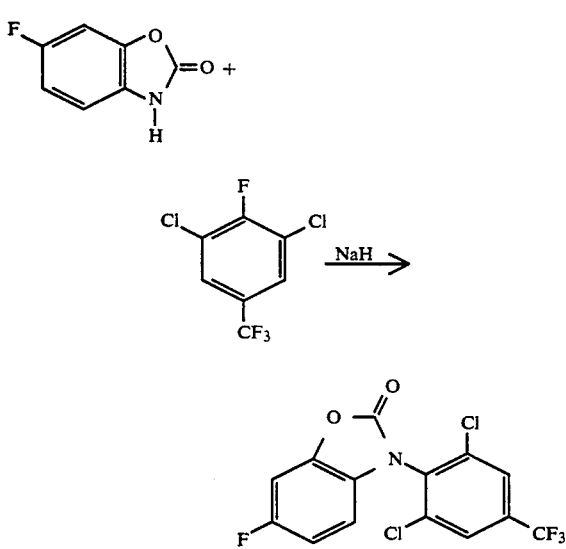

1.0 g (0.0065M) of the intermediate 6-fluoro-2-benzoxazolinone was added to a mixture of 10.0 ml dimethylformamide and 0.3 g (0.013 M) sodium hydride. The mixture was stirred at 40° C. for 30 minutes. 1.7 g (7.0 mmole) 3,5-dichloro-4-fluorobenzotrifluoride was added, and the mixture was stirred to 3.0 hours. After 3.0 hours the temperature was raised to 70° C. for another 3.0 hours. The mixture was cooled, and a few drops of methanol was added to the mixture. The mixture was poured into a cold 30 ml 2% solution of hydrogen chloride. The mixture was extracted with methylene chloride and washed again with 2% hydrogen chloride solution.

The organic phase was separated, dried with anhydrous magnesium sulfate and stripped in vacuum. The resulting 1.4 g dark semi-solid was purified by chromatography (Silica gel, Hexane/ethyl acetate elution). 1.0 g orange material was retrieved. Spectroscopic data: nuclear magnetic resonance (NMR), C-13 NMR, infrared and mass spectroscopy are consistent with the proposed structure.

EXAMPLE 2

5-ethyl-3-(3'-chloro-5'-trifluoro-2-pyridyl)-2-benzoxazolinone Compound 14 in Table I

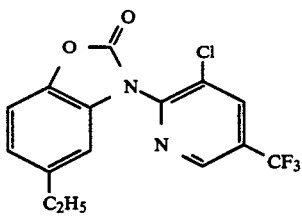

Step 1: Preparation of the intermediate; 5-ethyl-2-benzoxazolinone

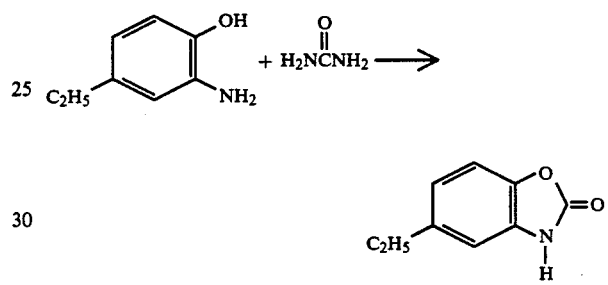

8.2 g (0.06 M) 2-amino-4-ethylphenol and 5.4 g (0.09 M) urea were thoroughly mixed and heated in an oil bath to 180° C. for 2.0 hours. Thereafter the mixture was allowed to cool to 100° C. HCl solution (1.0 normal) was added to the mixture while stirring and the mixture was cooled to room temperature. The cooled mixture was extracted three times with methylene chloride. The combined organic phases were dried and stripped in vacuum. The sample yielded 5.9 g dark solid with a melting point of 75°-77° C. Spectroscopic data: nuclear magnetic resonance (NMR), C-13 NMR, infrared, and mass spectroscopy are consistent with the proposed structure.

Step 2: Arylation of the 5-ethyl-2-benzoxazolinone

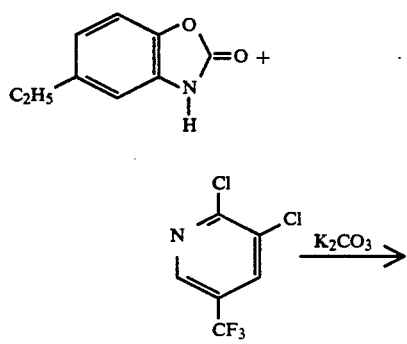

-continued

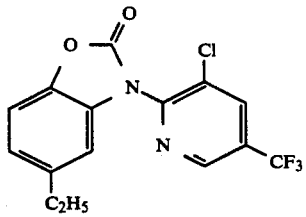

A mixture containing 50 ml dimethylformamide, 4.2 g (0.03 M) anhydrous $K_2CO_3$, 150 mg 18-crown-5 ether, 2.0 g (0.012 M) 5-ethyl-2-benzoxazolinone (from Step 1) and 2.4 g (0.012 M) 2,3-dichloro-5-trifluoroethylpyridine were stirred and heated to 100° C. for 3.0 hours and then cooled. The mixture was stirred with methylene chloride and water.

The organic phase was separated, dried over anhydrous magnesium sulfate and stripped. The sample yielded 4.0 g of a dark semi-solid. Spectroscopic data: nuclear magnetic resonance (NMR), C-13 NMR, infrared, and mass spectroscopy are consistent with the proposed structure.

The following Table I depicts representative compounds of this invention.

TABLE I
COMPOUNDS

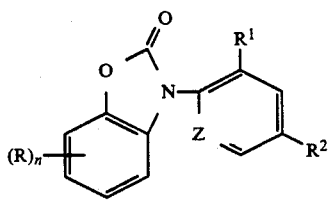

| Compound No. | R | $R^1$ | $R^2$ | Z | $R^3$ |
|---|---|---|---|---|---|
| 1 | H | Cl | $CF_3$ | N | |
| 2 | H | Cl | $CF_3$ | C | Cl |
| 3 | 5-Cl | Cl | $CF_3$ | N | |
| 4 | 5-Cl | Cl | $CF_3$ | C | Cl |
| 5 | 6-$NO_2$ | Cl | $CF_3$ | C | Cl |
| 6 | 6-$OCH_3$ | Cl | $CF_3$ | C | Cl |
| 7 | 5-$NO_2$ | Cl | $CF_3$ | C | Cl |
| 8 | 6-$OCH_3$ | Cl | $CF_3$ | N | |
| 9 | 5-$CO_2CH_3$ | Cl | $CF_3$ | C | Cl |
| 10 | 6-$CH_3$ | Cl | $CF_3$ | C | Cl |
| 11 | 6-$CH_3$ | Cl | $CF_3$ | N | |
| 12 | 6-$CO_2CH_3$ | Cl | $CF_3$ | C | Cl |
| 13 | 5-$C_2H_5$ | Cl | $CF_3$ | C | Cl |
| 14 | 5-$C_2H_5$ | Cl | $CF_3$ | N | |
| 15 | 6-F | Cl | $CF_3$ | C | Cl |

Herbicidal Screening Tests

The compounds listed in the foregoing table were tested for herbicidal activity by various methods and at various rates of application. The results of some of these tests are given below. As one skilled in the art is aware, the results obtained in herbicidal screening tests are affected by a number of factors that are not readily controllable. Environmental conditions, such as amount of sunlight and water, soil type, soil pH, temperature and humidity, are examples of such factors. Other factors which can affect test results are the depth of planting and the application rate of the herbicide, as well as the nature of the crops being tested. Results will also vary from crop to crop and within the crop varieties.

Pre-emergence Herbicidal Screening Test

On the day preceding treatment, seeds of several different weed species were planted in sandy loam soil in individual rows using one species per row across the width of a flat. The grassy weeds planted were green foxtail (*Setaria viridis*), wild oat (*Avena futua*), and barnyard grass (*Echinochloa crusgalli*). Broadleaf weeds utilized were wild mustard (*Brassica kaber*), velvetleaf (*Abutilon theophrasti*), and annual morningglory (*Ipomoea spp.*). Additionally, yellow nutsedge (*Cyperus esculentus*) was planted. Ample seeds were planted to give about 20 to 40 seedlings per row, after emergence, depending upon the size of the plants.

Solutions of the test compounds were made by weighing out 74.7 (mg) of the test compound into a 60 ml wide-mouth bottle, then dissolving the compound in 7 ml acetone containing 1% Tween 20 (polyoxyethylene sorbitan monolaurate emulsifier). Additional solvents, not exceeding 5 ml, were used if needed to dissolve the compound. A 20.5 ml aliquot was then taken from the solution and diluted with 25 ml of an acetone:water mixture (19:1) containing 1% Tween 20 to form a sprayable solution.

The flats were placed in a greenhouse at 21°-29.5° C., and watered by sprinkling. One day after planting, the flats were sprayed with the spray solution calibrated to deliver 748L/ha. The application rate was 4.0 kg/ha.

The flats were then returned to the greenhouse and water daily by sprinkling. The degree of weed control was estimated and recorded 17 to 21 days after treatment, as percentage control compared to the growth of the same species in an untreated check flat of the same age.

The percent control is the total injury to the plants due to all factors, including inhibited germination, killing of the plant tissue after emergence, stunting, malformation, chlorosis and other types of injury. The control ratings vary from 0 to 100 percent, where 0 represents no effect with growth equal to the untreated control, and 100 represents complete kill; a dash indicates that no test was performed at that level of application.

Post-emergence Herbicidal Evaluation

The soil was prepared and seeded with the same varieties as described for the pre-emergence test. The flats were placed in the greenhouse at 21°-29° C. and watered by sprinkling. The seeds of the weed species were planted 10 to 12 days before treatment. Plants were sprayed 30.5 cm above the foliage and the application rate was 4 kg/ha, using a spray solution as prepared in the pre-emergence test. Grasses were sprayed at a 3 to 4 leaf stage and broadleaves at a 1 to 2 leaf stage. Yellow nutsedge was 5 to 7 cm tall at time of application.

The flats were returned to the greenhouse after spraying and watered daily without wetting the foliage. Three weeks after treatment the degree of weed control was estimated and recorded as percentage control compared to the growth of the same species in an untreated check flat of the same age. The percent control ratings were assigned on the basis as for the pre-emergence evaluation.

Table II lists the results of these tests, in terms of averages for the grasses and broadleaf weeds, with yellow nutsedge listed separately, in both pre- and post-emergence evaluations.

TABLE II

Pre-emergence and Post-emergence Herbicidal Activity
Application Rate - 4.0 kg/ha Abbreviations:
- AVG: Grass weeds averaged
- AVB: Broadleaf weeds averaged
- YNS: Yellow Nutsedge

| Compound No | Pre-Emergence AVG | Pre-Emergence AVB | Pre-Emergence YNS | Post-Emergence AVG | Post-Emergence AVB | Post-Emergence YNS |
| --- | --- | --- | --- | --- | --- | --- |
| 1 | 10 | 63 | 0 | 56 | 73 | 0 |
| 2 | 58 | 38 | 0 | 10 | 65 | 0 |
| 3 | 0 | 0 | 0 | 6 | 20 | 0 |
| 4 | 0 | 0 | 0 | 3 | 3 | 0 |
| 5 | 91 | 76 | 5 | 16 | 86 | 0 |
| 6 | 26 | 36 | 0 | 5 | 53 | 0 |
| 7 | 0 | 0 | 0 | 6 | 20 | 0 |
| 8 | 0 | 3 | 0 | 3 | 5 | 0 |
| 9 | 38 | 70 | 0 | 10 | 56 | 0 |
| 10 | 16 | 61 | 0 | 3 | 45 | 0 |
| 11 | 63 | 63 | 5 | 40 | 76 | 5 |
| 12 | 0 | 36 | 0 | 5 | 8 | 0 |
| 13 | 36 | 75 | 0 | 8 | 73 | 0 |
| 14 | 60 | 65 | 0 | 20 | 71 | 5 |
| 15 | 86 | 96 | 0 | 71 | 100 | 5 |

The compounds of the present invention are useful as herbicides and can be applied in a variety of ways known to those skilled in the art, at various concentrations. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as amount 95% or more by weight of active ingredient. The optimum amount for any given compound will depend upon the nature of the seeds or plants to be controlled. The rate of application will generally vary from about 0.01 to about 10 pounds per acre, preferably from about 0.02 to about 4 pounds per acre.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the entire capsule, and may include solvent in addition to the active compound.

Encapsulated granules are characterized by porous membranes sealing the openings of the granule carrier pores, trapping the liquid containing the active components inside for controlled release. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier, such as the Freons, may also be used.

Many of these formulations include wetting, dispersing or emulsifying agents. Examples are alkyl and alkyl-aryl sulfonates and sulfates and their salts; polyhydric alcohols; polyethoxylated alcohols; esters and fatty amines. These agents when used normally comprise from 0.1% to 15% by weight of the formulation.

Each of the above formulations can be prepared as a package containing the herbicide together with other ingredients of the formulation (diluents, emulsifiers, surfactants etc.). The formulations can also be prepared by a tank mix method, in which the ingredients are obtained separately and combined at the grower site.

The compounds of the present invention are also useful when combined with other herbicides and/or defoliants, dessicants, growth inhibitors, and the like. These other materials can comprise from about 5% to about 95% of the active ingredients in the formulations. These combinations frequently provided a higher level of effectiveness in controlling weeds and often provide results unattainable with separate formulations of the individual herbicides.

Examples of other herbicides, defoliants, dessicants and plant growth inhibitors with which the compounds of this invention can be combined are:

acetanilide herbicides such as alachlor, 2-chloro-2',6'-diethyl-N-(methoxymethyl) acetanilide; acetochlor, 2-chloro-2'-methyl-6'ethyl-N-ethoxymethyl acetanilide; metolachlor, 2-chloro-2'-methyl-6'ethyl-N-methoxy-isopropyl-2-acetanilide;

chlorophenoxy herbicides such as 2,4-D, 2,4,5-T, MCPA, MCPB, 2,4-DB, 2,4-DEB, 4-CPA, 2,4,5-TB, and silvex;

carbamate herbicides such as propham, chlorpropham, swep, and barban;

thiocarbamate and dithiocarbamate herbicides such as CDEC, metham-sodium, EPTC, diallate, PEBC, and vernolate;

substituted urea herbicides such as norea, dichloral, urea, chloroxuron, cycluron, fenuron, monuron, monuron TCA, diuron, linuron, monolinuron neburon, buturon and trimeturon;

substituted triazine herbicides such as simazine, chlorazine, desmetryne, norazine, ipazine, prometryn, atrazine, trietazine, simetone, prometone, propazine and ametryne;

chlorinated aliphatic acid herbicides such as TCA and dalapon;

chlorinated benzoic acid and phenylacetic acid herbicides such as 2,3,6-TBA, dicamba, tricamba, chloramben, fenac, PBA, 2-methoxy-3,6-dichlorophenyl acetic acid, 3-methoxy-2,6-dichlorophenyl acetic acid, 2-methoxy-3,5,6-trichlorophenyl acetic acid, and 2,4-dichloro-3-nitro benzoic acid;

and such compounds as aminotriazole, maleic hydrazide, phenylmercury acetate, endothal, technical chlordane, CDCPA, diquat, erbon, DNC, DNBP, dichlobenil, DPA, diphenamide, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, sesone, terbacil, terbutol, TCBA, nitralin, sodium tetraborate, calcium cyanamide, S,S,S-tributylphosphorotrithioate and propanil, isopropyl amine salt of N-phosphonomethyl glycine, trimethylsulfonium salts of N-phosphonomethyl glycine.

These formulations can be applied to the areas where control is desired by conventional methods. Dust and liquid compositions, for example, can be applied by the use of powerdusters, boom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

The following are examples of typical formulations.

| 5% dust: | 5 parts active compound |
|---|---|
| | 95 parts talc |
| 2% dust: | 2 parts active compound |
| | 1 part highly dispersed silicic acid |
| | 97 parts talc |

These dusts are formed by mixing the components then grinding the mixture to the desired particle size.

| 5% granules: | 5 parts active compound |
|---|---|
| | 0.25 part epichlorohydrin |
| | 0.25 part cetyl polyglycol ether |
| | 3.5 parts polyethylene glycol |
| | 91 part kaolin (particle size 0.3–0.8 mm) |

Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo.

| Wettable powders: | |
|---|---|
| 70%: | 70 parts active compound |
| | 5 parts sodium dibutylnaphthylsulfonate |
| | 3 parts naphthalenesulfonic acid/phenolsulfonic acid/formaldehyde condensate (3:2:1) |
| | 10 parts kaolin |
| | 12 parts Champagne chalk |
| 40%: | 40 parts active compound |
| | 5 parts sodium lignin sulfonate |
| | 1 part sodium dibutylnaphthalene sulfonic acid |
| | 54 parts silicic acid |
| 25%: | 25 parts active compound |
| | 4.5 parts calcium lignin sulfate |
| | 1.9 parts Champagne chalk/hydroxyethyl cellulose (1:1) |
| | 1.5 parts sodium dibutylnaphthalene sulfonate |
| | 19.5 silicic acid |
| | 19.5 parts Champagne chalk |
| | 28.1 parts kaolin |
| 25%: | 25 parts active compound |
| | 2.5 parts isooctylphenoxy-polyethyleneethanol |
| | 1.7 parts Champagne chalk/hydroxyethyl cellulose (1:1) |
| | 8.3 parts sodium aluminum silicate |
| | 16.5 parts kieselguhr |
| | 46 parts kaolin |
| 10%: | 10 parts active compound |
| | 3 parts of a mixture of sodium salts of saturated fatty alcohol sulfates |
| | 5 parts naphthalenesulfonic acid/formaldehyde condensate |
| | 82 parts kaolin |

These wettable powders are prepared by intimately mixing the active compounds with the additives in suitable mixers, and grinding the resulting mixture in mills or rollers.

| Emulsifiable concentrate: | |
|---|---|
| 25%: | 25 parts active substance |
| | 2.5 parts epoxidized vegetable oil |
| | 10 parts of an alkylarylsulfonate/fatty alcohol polyglycol ether mixture |
| | 5 parts dimethylformamide |
| | 57.5 parts xylene |

What is claimed is:

1. A compound having the formula

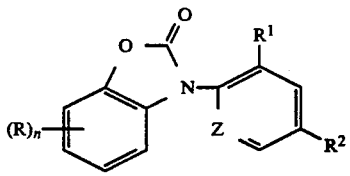

in which:

R is hydrogen, alkyl, alkoxy, alkenyloxy, alkynyloxy, carboxyalkoxy, alkoxycarbonylalkoxy, alkoxyalkoxy, cyanoalkoxy, haloalkysulphonylamino, alkysulphonylamino, alkoxycarbonyl, haloalkyl, halogen, nitro, carboxy, carboxyalkyl, hydroxy, benzyloxy and cyano;

n is 0, 1, 2, or 3;

R¹ is hydrogen, halogen, cyano, haloalkyl, alkyl, alkyoxy, or alkythio;

R² is halogen, haloalkyl, haloalkyoxy; and

Z is N or C—R₃, wherein R₃ is hydrogen, halogen, nitro, cyano, alkythio, alkoxy or haloalkyl.

2. A compound according to claim 1 wherein R is halogen, alkyl, alkoxy, nitro or carboxyalkyl, n is 1 or 2.

3. A compound according to claim 2 wherein R¹ is halogen and R² is haloalkyl.

4. A compound according to claim 3 wherein Z is N.

5. A compound according to claim 3 wherein Z is C—R₃

6. A compound according to claim 5 wherein R₃ is halogen.

7. A compound according to claim 4 wherein R is chloro, fluoro, methyl, ethyl, nitro, methoxy, ethoxy or methoxycarbonyl.

8. A compound according to claim 5 wherein R is chloro, fluoro, methyl, ethyl, nitro, methoxy, ethoxy or methoxycarbonyl.

9. A compound according to claim 4 wherein R is substituted at the 5- or 6-position.

10. A compound according to claim 5 wherein R is substituted at the 5- or 6-position.

11. An herbicidal composition comprising an inert diluent and an herbicidally effective amount of a compound having the formula

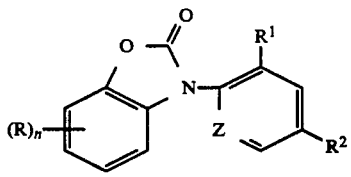

in which:

R is hydrogen, alkyl, alkoxy, alkenyloxy, alkynyloxy, carboxyalkoxy, alkoxycarbonylalkoxy, alkoxyalkoxy, cyanoalkoxy, haloalkysulphonylamino, alkysulphonylamino, alkoxycarbonyl, haloalkyl, halogen, nitro, carboxy, carboxyalkyl, hydroxy, benzyloxy and cyano;

n is 0, 1, 2, or 3;

R¹ is hydrogen, halogen, cyano, haloalkyl, alkyl, alkyoxy, or alkythio;

R² is halogen, haloalkyl, haloalkyoxy; and

Z is N or C—R₃, wherein R₃ is hydrogen, halogen, nitro, cyano, alkythio, alkoxy or haloalkyl.

12. A composition according to claim 11 wherein R is halogen, alkyl, alkoxy, nitro or carboxyalkyl, n is 1 or 2.

13. A composition according to claim 12 wherein R¹ is halogen and R² is haloalkyl.

14. A composition according to claim 13 wherein Z is N.

15. A composition according to claim 13 wherein Z is C—R₃.

16. A composition according to claim 15 wherein R₃ is halogen.

17. A composition according to claim 14 wherein R is chloro, fluoro, methyl, ethyl, nitro, methoxy, ethoxy or methoxycarbonyl.

18. A composition according to claim 15 wherein R is chloro, fluoro, methyl, ethyl, nitro, methoxy, ethoxy or methoxycarbonyl.

19. A composition according to claim 14 wherein R is substituted at the 5- or 6-position.

20. A composition according to claim 15 wherein R is substituted at the 5- or 6-position.

21. The method of controlling undesirable vegetation comprising applying to the area where control is desired, an herbicidally effective amount of a compound having the formula

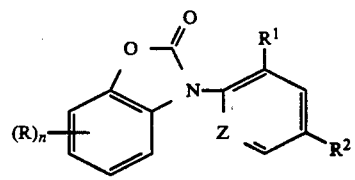

in which:

R is hydrogen, alkyl, alkoxy, alkenyloxy, alkynyloxy, carboxyalkoxy, alkoxycarbonylalkoxy, alkoxyalkoxy, cyanoalkoxy, haloalkysulphonylamino, alkysulphonylamino, alkoxycarbonyl, haloalkyl, halogen, nitro, carboxy, carboxyalkyl, hydroxy, benzyloxy and cyano;

n is 0, 1, 2, or 3;

R¹ is hydrogen, nitro, halogen, cyano, haloalkyl, alkyl, alkyoxy, and alkythio;

R² is hydrogen, halogen, haloalkyl, haloalkyoxy, nitro and cyano; and

Z is N or C—R₃, wherein R₃ is hydrogen, halogen, nitro, cyano, alkythio, alkoxy and haloalkyl.

* * * * *